(12) United States Patent
Xiong et al.

(10) Patent No.: US 10,473,593 B1
(45) Date of Patent: Nov. 12, 2019

(54) SYSTEM AND METHOD FOR DAMAGE DETECTION BY CAST SHADOWS

(71) Applicant: United Technologies Corporation, Farmington, CT (US)

(72) Inventors: Ziyou Xiong, Wethersfield, CT (US); Alan Matthew Finn, Hebron, CT (US)

(73) Assignee: United Technologies Corporation, Farmington, CT (US)

( * ) Notice: Subject to any disclaimer, the term of this patent is extended or adjusted under 35 U.S.C. 154(b) by 0 days.

(21) Appl. No.: 15/971,227

(22) Filed: May 4, 2018

(51) Int. Cl.
*G01B 11/08* (2006.01)
*G01N 21/88* (2006.01)
*G06T 7/00* (2017.01)

(52) U.S. Cl.
CPC ..... *G01N 21/8806* (2013.01); *G01N 21/8851* (2013.01); *G06T 7/001* (2013.01); *G01N 2021/8829* (2013.01)

(58) Field of Classification Search
CPC ........... G01N 21/8806; G01N 21/8851; G01N 2021/8829; G06T 7/001
See application file for complete search history.

(56) References Cited

U.S. PATENT DOCUMENTS

| | | | |
|---|---|---|---|
| 3,804,397 A | 4/1974 | Neumann | |
| 4,402,053 A | 8/1983 | Kelley et al. | |
| 4,403,294 A * | 9/1983 | Hamada | G01N 21/88 250/559.08 |
| 4,873,651 A * | 10/1989 | Raviv | G06T 1/0014 700/259 |
| 5,064,291 A * | 11/1991 | Reiser | G01N 21/95684 356/625 |
| 5,119,678 A | 6/1992 | Bashyam et al. | |
| 5,345,514 A | 9/1994 | Mandavieh et al. | |
| 5,345,515 A * | 9/1994 | Nishi | D01G 31/00 356/238.3 |
| 5,351,078 A * | 9/1994 | Lemelson | H04N 5/7822 348/130 |
| 5,963,328 A * | 10/1999 | Yoshida | G01N 21/8806 356/237.2 |

(Continued)

FOREIGN PATENT DOCUMENTS

CA  2820732 A1  12/2014
DE  19710743 A1  9/1998

(Continued)

OTHER PUBLICATIONS

U.S. Final Office Action dated Jan. 3, 2019 for corresponding U.S. Appl. No. 15/971,254.

(Continued)

*Primary Examiner* — Roy M Punnoose
(74) *Attorney, Agent, or Firm* — Bachman & LaPointe, P.C.

(57) ABSTRACT

An inspection system comprises an imaging device mounted so as to image a component surface. At least one controllable light mounted at low oblique angles around the component and configured to illuminate the component surface and cast at least one shadow on the component surface. A processor is coupled to the imaging device and the at least one controllable light. The processor is used for determining a feature based on a dissimilarity between image data and a reference model, and to determine damage to the component.

16 Claims, 3 Drawing Sheets

(56) References Cited

U.S. PATENT DOCUMENTS

| | | | |
|---|---|---|---|
| 6,153,889 A | 11/2000 | Jones | |
| 6,177,682 B1 * | 1/2001 | Bartulovic | G01N 21/951 250/559.12 |
| 6,399,948 B1 | 6/2002 | Thomas | |
| 6,434,267 B1 | 8/2002 | Smith | |
| 6,462,813 B1 | 10/2002 | Haven et al. | |
| 6,759,659 B2 | 7/2004 | Thomas et al. | |
| 6,804,622 B2 | 10/2004 | Bunker et al. | |
| 6,907,358 B2 | 6/2005 | Suh et al. | |
| 6,965,120 B1 * | 11/2005 | Beyerer | G01N 21/8806 250/559.39 |
| 7,026,811 B2 | 4/2006 | Roney, Jr. et al. | |
| 7,064,330 B2 | 6/2006 | Raulerson et al. | |
| 7,119,338 B2 | 10/2006 | Thompson et al. | |
| 7,122,801 B2 | 10/2006 | Favro et al. | |
| 7,164,146 B2 | 1/2007 | Weir et al. | |
| 7,190,162 B2 | 3/2007 | Tenley et al. | |
| 7,233,867 B2 | 6/2007 | Pisupati et al. | |
| 7,240,556 B2 | 7/2007 | Georgeson et al. | |
| 7,272,529 B2 | 9/2007 | Hogan et al. | |
| 7,313,961 B2 | 1/2008 | Tenley et al. | |
| 7,415,882 B2 | 8/2008 | Fetzer et al. | |
| 7,446,886 B2 * | 11/2008 | Aufmuth | G01B 11/30 356/601 |
| 7,489,811 B2 | 2/2009 | Brummel et al. | |
| 7,602,963 B2 | 10/2009 | Nightingale et al. | |
| 7,689,030 B2 | 3/2010 | Suh et al. | |
| 7,724,925 B2 | 5/2010 | Shepard | |
| 7,738,725 B2 | 6/2010 | Raskar et al. | |
| 7,823,451 B2 | 11/2010 | Sarr | |
| 7,966,883 B2 | 6/2011 | Lorraine et al. | |
| 8,204,294 B2 | 6/2012 | Alloo et al. | |
| 8,208,711 B2 | 6/2012 | Venkatachalam et al. | |
| 8,221,825 B2 | 7/2012 | Reitz et al. | |
| 8,239,424 B2 | 8/2012 | Haigh et al. | |
| 8,431,917 B2 | 4/2013 | Wang et al. | |
| 8,449,176 B2 | 5/2013 | Shepard | |
| 8,520,931 B2 | 8/2013 | Tateno | |
| 8,528,317 B2 | 9/2013 | Gerez et al. | |
| 8,692,887 B2 | 4/2014 | Ringermacher et al. | |
| 8,744,166 B2 | 6/2014 | Scheid et al. | |
| 8,761,490 B2 | 6/2014 | Scheid et al. | |
| 8,781,209 B2 | 7/2014 | Scheid et al. | |
| 8,781,210 B2 | 7/2014 | Scheid et al. | |
| 8,792,705 B2 | 7/2014 | Scheid et al. | |
| 8,913,825 B2 | 12/2014 | Taguchi et al. | |
| 8,983,794 B1 | 3/2015 | Motzer et al. | |
| 9,037,381 B2 | 5/2015 | Care | |
| 9,046,497 B2 | 6/2015 | Kush et al. | |
| 9,080,453 B2 | 7/2015 | Shepard et al. | |
| 9,116,071 B2 | 8/2015 | Hatcher, Jr. et al. | |
| 9,134,280 B2 | 9/2015 | Cataldo et al. | |
| 9,146,205 B2 | 9/2015 | Renshaw et al. | |
| 9,151,698 B2 | 10/2015 | Jahnke et al. | |
| 9,154,743 B2 | 10/2015 | Hatcher, Jr. et al. | |
| 9,251,582 B2 | 2/2016 | Lim et al. | |
| 9,300,865 B2 | 3/2016 | Wang et al. | |
| 9,305,345 B2 | 4/2016 | Lim et al. | |
| 9,458,735 B1 | 10/2016 | Diwinsky et al. | |
| 9,465,385 B2 | 10/2016 | Kamioka et al. | |
| 9,467,628 B2 | 10/2016 | Geng et al. | |
| 9,471,057 B2 | 10/2016 | Scheid et al. | |
| 9,476,798 B2 | 10/2016 | Pandey et al. | |
| 9,476,842 B2 | 10/2016 | Drescher et al. | |
| 9,483,820 B2 | 11/2016 | Lim et al. | |
| 9,488,592 B1 | 11/2016 | Maresca et al. | |
| 9,519,844 B1 | 12/2016 | Thompson et al. | |
| 9,594,059 B1 | 3/2017 | Brady et al. | |
| 9,734,568 B2 | 5/2017 | Vajaria et al. | |
| 9,785,919 B2 | 10/2017 | Diwinsky et al. | |
| 9,804,997 B2 | 10/2017 | Sharp et al. | |
| 9,808,933 B2 | 11/2017 | Lin et al. | |
| 2002/0121602 A1 | 9/2002 | Thomas et al. | |
| 2002/0167660 A1 * | 11/2002 | Zaslavsky | G01N 21/8806 356/237.2 |
| 2003/0117395 A1 | 6/2003 | Yoon | |
| 2003/0205671 A1 | 11/2003 | Thomas et al. | |
| 2004/0089811 A1 | 5/2004 | Lewis et al. | |
| 2004/0089812 A1 | 5/2004 | Favro et al. | |
| 2004/0139805 A1 | 7/2004 | Antonelli et al. | |
| 2004/0201672 A1 | 10/2004 | Varadarajan et al. | |
| 2004/0240600 A1 | 12/2004 | Freyer et al. | |
| 2004/0245469 A1 | 12/2004 | Favro et al. | |
| 2004/0247170 A1 * | 12/2004 | Furze | G01B 11/25 382/141 |
| 2005/0008215 A1 | 1/2005 | Shepard | |
| 2005/0151083 A1 | 7/2005 | Favro et al. | |
| 2005/0167596 A1 | 8/2005 | Rothenfusser et al. | |
| 2007/0017297 A1 | 1/2007 | Georgeson et al. | |
| 2007/0045544 A1 | 3/2007 | Favro et al. | |
| 2008/0022775 A1 | 1/2008 | Sathish et al. | |
| 2008/0053234 A1 | 3/2008 | Staroselsky et al. | |
| 2008/0183402 A1 | 7/2008 | Malkin et al. | |
| 2008/0229834 A1 | 9/2008 | Bossi et al. | |
| 2008/0247635 A1 | 10/2008 | Davis et al. | |
| 2008/0247636 A1 | 10/2008 | Davis et al. | |
| 2009/0000382 A1 | 1/2009 | Sathish et al. | |
| 2009/0010507 A1 | 1/2009 | Geng | |
| 2009/0066939 A1 | 3/2009 | Venkatachalam et al. | |
| 2009/0128643 A1 | 5/2009 | Kondo et al. | |
| 2009/0252987 A1 | 10/2009 | Greene, Jr. | |
| 2009/0279772 A1 | 11/2009 | Sun et al. | |
| 2009/0312956 A1 | 12/2009 | Zombo et al. | |
| 2011/0062339 A1 | 3/2011 | Ruhge et al. | |
| 2012/0154599 A1 | 6/2012 | Huang | |
| 2012/0275667 A1 | 11/2012 | Lu | |
| 2012/0293647 A1 | 11/2012 | Singh et al. | |
| 2013/0028478 A1 | 1/2013 | St-Pierre et al. | |
| 2013/0070897 A1 | 3/2013 | Jacotin | |
| 2013/0235897 A1 | 9/2013 | Bouteyre et al. | |
| 2013/0250067 A1 | 9/2013 | Laxhuber et al. | |
| 2014/0022357 A1 | 1/2014 | Yu et al. | |
| 2014/0056507 A1 | 2/2014 | Doyle et al. | |
| 2014/0098836 A1 | 4/2014 | Bird | |
| 2014/0184786 A1 | 7/2014 | Georgeson et al. | |
| 2014/0198185 A1 | 7/2014 | Haugen et al. | |
| 2014/0200832 A1 | 7/2014 | Troy et al. | |
| 2015/0041654 A1 | 2/2015 | Barychev et al. | |
| 2015/0046098 A1 | 2/2015 | Jack et al. | |
| 2015/0086083 A1 | 3/2015 | Chaudhry et al. | |
| 2015/0128709 A1 | 5/2015 | Stewart et al. | |
| 2015/0138342 A1 | 5/2015 | Brdar et al. | |
| 2015/0185128 A1 | 7/2015 | Chang et al. | |
| 2015/0253266 A1 | 9/2015 | Lucon et al. | |
| 2016/0012588 A1 | 1/2016 | Taguchi et al. | |
| 2016/0043008 A1 | 2/2016 | Murray et al. | |
| 2016/0109283 A1 | 4/2016 | Broussais-Colella et al. | |
| 2016/0178532 A1 | 6/2016 | Lim et al. | |
| 2016/0241793 A1 | 8/2016 | Ravirala et al. | |
| 2016/0314571 A1 | 10/2016 | Finn et al. | |
| 2016/0328835 A1 | 11/2016 | Maresca, Jr. et al. | |
| 2017/0011503 A1 | 1/2017 | Newman | |
| 2017/0023505 A1 | 1/2017 | Malone et al. | |
| 2017/0052152 A1 | 2/2017 | Tat et al. | |
| 2017/0085760 A1 * | 3/2017 | Ernst | H04N 5/2256 |
| 2017/0090458 A1 | 3/2017 | Lim et al. | |
| 2017/0122123 A1 | 5/2017 | Kell et al. | |
| 2017/0184469 A1 | 6/2017 | Chang et al. | |
| 2017/0184549 A1 | 6/2017 | Reed et al. | |
| 2017/0184650 A1 | 6/2017 | Chang et al. | |
| 2017/0221274 A1 | 8/2017 | Chen et al. | |
| 2017/0234837 A1 | 8/2017 | Hall et al. | |
| 2017/0258391 A1 | 9/2017 | Finn et al. | |
| 2017/0262965 A1 | 9/2017 | Xiong et al. | |
| 2017/0262977 A1 | 9/2017 | Finn et al. | |
| 2017/0262979 A1 | 9/2017 | Xiong et al. | |
| 2017/0262985 A1 | 9/2017 | Finn et al. | |
| 2017/0262986 A1 | 9/2017 | Xiong et al. | |
| 2017/0270651 A1 | 9/2017 | Bailey et al. | |
| 2017/0297095 A1 | 10/2017 | Zalameda et al. | |
| 2018/0002039 A1 * | 1/2018 | Finn | B64F 5/60 |
| 2018/0005362 A1 | 1/2018 | Wang et al. | |

(56) References Cited

U.S. PATENT DOCUMENTS

| | | | |
|---|---|---|---|
| 2018/0019097 A1* | 1/2018 | Harada | G01B 15/04 |
| 2018/0098000 A1 | 4/2018 | Park et al. | |
| 2018/0111239 A1 | 4/2018 | Zak et al. | |

FOREIGN PATENT DOCUMENTS

| | | |
|---|---|---|
| EP | 1961919 A2 | 8/2008 |
| GB | 2545271 A | 6/2017 |
| JP | 2015161247 A | 9/2015 |
| SG | 191452 A1 | 7/2013 |
| WO | 2016112018 A1 | 7/2016 |
| WO | 2016123508 A1 | 8/2016 |
| WO | 2016176524 A1 | 11/2016 |

OTHER PUBLICATIONS

Gao et al., 'A Statistical Method for Crack Detection from Vibrothermography Inspection Data',(2010) Statistics Preprints. Paper 68. http://lib.dr.iastate.edu/stat_las_preprints/68.

Li1 Ming; Holland1 Stephen D.; and Meeker1 William Q.1 "Statistical Methods for Automatic Crack Detection Based on Vibrothermography Sequence-of-Images Data" (2010). Statistics Preprints. 69.

Henneke et al. 'Detection of Damage in Composite Materials by Vibrothermography', ASTM special technical publication (696), American Society for Testing and Materials, 1979, pp. 83-95.

http://www.npl.co.uk/commercial-services/sector-case-studies/thermal-imaging-reveals-the-invisible; Apr. 17, 2012.

Tian et al., 'A Statistical Framework for Improved Automatic Flaw Detection in Nondestructive Evaluation Images', Technometrics, 59, 247-261. Feb. 1, 2017.

Emmanuel J. Cand'es1,2, Xiaodong Li2, Yi MA3,4, and John Wright4, "Robust Principal Component Analysis", (1)Department of Statistics, Stanford University, Stanford, CA; (2)Department of Mathematics, Stanford University, Stanford, CA; (3, 4) Electrical and Computer Engineering, UIUC, Urbana, IL (4) Microsoft Research Asia, Beijing, China, Dec. 17, 2009.

Sebastien Parent; "From Human to Machine: How to Be Prepared for Integration of Automated Visual Inspection" Quality Magazine, https://www.qualitymag.com/articles/91976. Jul. 2, 2014.

http://www.yxlon.com/products/x-ray-and-ct-inspection-systems/yxlon-mu56-tb, 2016.

U.S. Office action dated Jul. 23, 2018 issued in corresponding U.S. Appl. No. 15/971,254.

Blachnio et al, "Assessment of Technical Condition Demonstrated by Gas Turbine Blades by Processing of Images of Their Surfaces", Journal of KONBiN, 1(21), 2012, pp. 41-50.

Raskar et al., 'A Non-photorealistic Camera: Depth Edge Detection and Stylized Rendering using Multi-flash Imaging' ACM Transactions on Graphics, 2004 http://www.merl.com/publications/docs/TR2006-107.pdf.

Feris et al., 'Specular Reflection Reduction with Multi-Flash Imaging', 17th Brazilian Symposium on Computer Graphics and Image Processing, 2004. http://rogerioferis.com/publications/FerisSIB04.pdf.

Holland, "First Measurements from a New Broadband Vibrothermography Measurement System", AIP Conference Proceedings, 894 (2007), pp. 478-483. http://link.aip.org/link/doi/10.1063/1.2718010 \.

Gao et al., 'Detecting Cracks in Aircraft Engine Fan Blades Using Vibrothermography Nondestructive Evaluation', RESS Special Issue on Accelerated Testing, 2014, http://dx.doi.org/10.1016/j.ress.2014.05.009.

Gao et al., 'A Statistical Method for Crack Detection from Vibrothermography Inspection Data', Statistics Preprints. Paper 68. http://lib.dr.iastate.edu/stat_las_preprints/68.

Holland, 'Thermographic Signal Reconstruction for Vibrothermography', Infrared Physics & Technology 54 (2011) 503-511.

Li et al., 'Statistical Methods for Automatic Crack Detection Based on Vibrothermography Sequence-of-Images Data', Statistics Preprints. Paper 69. http://lib.dr.iastate.edu/stat_las_preprints/69.

Tian et al., 'A Statistical Framework for Improved Automatic Flaw Detection in Nondestructive Evaluation Images', Technometrics, 59, 247-261.

Henneke et al. 'Detection of Damage in Composite Materials by Vibrothermography', ASTM special technical publication (696), 1979, pp. 83-95.

http://www.npl.co.uk/commercial-services/sector-case-studies/thermal-imaging-reveals-the-invisible.

E. J. Candès, X. Li, Y. Ma, and J. Wright, "Robust Principal Component Analysis", submitted. http://www-stat.stanford.edu/~candes/papers/RobustPCA.pdf.

M. Sznaier, O. Camps, N. Ozay, T. Ding, G. Tadmor and D. Brooks, "The Role of Dynamics in Extracting Information Sparsely Encoded in High Dimensional Data Streams", in Dynamics of Information Systems, Hirsch, M.J.; Pardalos, P. M.; Murphey, R. (Eds.), pp. 1-28, Springer Verlag, 2010.

M. Fazel, H. Hindi, and S. Boyd, "A Rank Minimization Heuristic with Application to Minimum Order System Approximation", American Control Conference, Arlington, Virginia, pp. 4734-4739, Jun. 2001.

Meola et al., 'An Excursus on Infrared Thermography Imaging', J. Imaging 2016, 2, 36 http://www.mdpi.com/2313-433X/2/4/36/pdf.

Yu et al., 'ASIFT: An Algorithm for Fully Affine Invariant Comparison', Image Processing on Line on Feb. 24, 2011. http://www.ipol.im/pub/art/2011/my-asift/article.pdf.

Schemmel et al., 'Measurement of Direct Strain Optic Coefficient of YSZ Thermal Barrier Coatings at Ghz Frequencies', Optics Express, v.25, n.17, Aug. 21, 2017, https://doi.org/10.1364/OE.25.019968.

Jean-Yves Bouguet, "Camera Calibration Toolbox for Matlab", http://www.vision.caltech.edu/bouguetj/calib_doc/, accessed on Nov. 10, 2017.

https://www.qualitymag.com/articles/91976-from-human-to-machine-how-to-be-prepared-for-integration-of-automated-visual-inspection.

http://www.yxlon.com/products/x-ray-and-ct-inspection-systems/yxlon-mu56-tb.

Yu et al. 'Shadow Graphs and 3D Texture Reconstruction', IJCV, vol. 62, No. 1-2, 2005, pp. 35-60.

U.S. Non-Final Office Action dated Apr. 16, 2019 for corresponding U.S. Appl. No. 15/970,985.

U.S. Non-Final Office Action dated May 28, 2019 for corresponding U.S. Appl. No. 15/971,214.

\* cited by examiner

SYSTEM AND METHOD FOR DAMAGE DETECTION BY CAST SHADOWS

BACKGROUND

The present disclosure is directed to an automated inspection system for detection of coating imperfections. Particularly, the disclosure is directed to an automated inspection system for detection of coating imperfections based on the method of "shape from shadows" (also called computational illumination or multi-flash imaging).

Gas turbine engine components, such as blades, vanes, disks, gears, and the like, may suffer irregularities during manufacture, such as spallation, machining defects, or inadequate coating, or may suffer wear and damage during operation, for example, due to erosion, hot corrosion (sulfidation), cracks, dents, nicks, gouges, and other damage, such as from foreign object damage. Detecting this damage may be achieved by images or videos for aircraft engine blade inspection, power turbine blade inspection, internal inspection of mechanical devices, and the like. A variety of techniques for inspecting by use of images or videos may include capturing and displaying images or videos to human inspectors for manual defect detection and interpretation. Human inspectors may then decide whether any defect exists within those images or videos. When human inspectors look at many similar images of very similar blades of an engine stage or like components of a device, they may not detect defects, for example, because of fatigue or distraction experienced by the inspector. Missing a defect may lead to customer dissatisfaction, transportation of an expensive engine back to service centers, lost revenue, or even engine failure. Additionally, manual inspection of components may be time consuming and expensive. Emerging 3D depth sensors might provide an alternative approach; however, it may be particularly difficult, time consuming, or expensive to directly 3D scan a component to an accuracy sufficient to detect shallow spallation or small manufacturing defects.

SUMMARY

In accordance with the present disclosure, there is provided an inspection system comprising an imaging device mounted so as to image a component surface; at least one controllable light mounted at low oblique angles around the component and configured to illuminate the component surface and cast shadows in a feature on the component surface; and a processor coupled to the imaging device and the at least one controllable light; the processor comprising a tangible, non-transitory memory configured to communicate with the processor, the tangible, non-transitory memory having instructions stored therein that, in response to execution by the processor, cause the processor to perform operations comprising: controlling, by the processor, the at least one controllable light to cast the shadows; receiving, by the processor, image data for the component from the imaging device; determining, by the processor, a feature based on a dissimilarity between the image data and a reference model; classifying, by the processor, the feature dissimilarity; and determining, by the processor, a probability that the feature dissimilarity indicates damage to the component.

In another and alternative embodiment, the inspection system further comprises removing specular reflections.

In another and alternative embodiment, the processor is further configured to control at least one of a position of said at least one controllable light and an orientation of said at least one controllable light, with respect to the component surface.

In another and alternative embodiment, controlling the at least one controllable light to cast the shadows further comprises illuminating the at least one controllable light independently.

In another and alternative embodiment, controlling the at least one controllable light to cast the shadows further comprises illuminating the component surface from multiple directions.

In another and alternative embodiment, the processor is further configured to compute a surface model from the image data to form a proxy model.

In another and alternative embodiment, the processor is further configured to determine a feature based on a dissimilarity between the image data and a proxy model.

In another and alternative embodiment, the imaging device is configured as at least one of a high dynamic range camera and a multi-polarization camera.

In another and alternative embodiment, the feature comprises a shallow surface defect.

In another and alternative embodiment, the feature comprises a coating imperfection.

In another and alternative embodiment, the at least one filter associated with the at least one controllable light and the imaging device wherein the at least one filter provides attenuation to at least one of intensity, frequency, and polarization.

In accordance with the present disclosure, there is provided a method for inspection of a component, comprising imaging a component surface with an imaging device; mounting one or more controllable lights at low oblique angles around the component; illuminating the component surface; casting one or more shadows in a feature on the component surface; and detecting a defect based on the shadows.

In another and alternative embodiment, the method for inspection of a component further comprises coupling a processor to the imaging device and the one or more controllable lights; the processor comprising a tangible, non-transitory memory configured to communicate with the processor, the tangible, non-transitory memory having instructions stored therein that, in response to execution by the processor, cause the processor to perform operations comprising: controlling the one or more controllable lights to cast the one or more shadows; receiving image data for the component from the imaging device; determining a feature based on dissimilarity between the image data and a reference model; classifying the feature; and determining a probability that the feature indicates damage to the component.

In another and alternative embodiment, the method for inspection of a component further comprises removing specular reflections.

In another and alternative embodiment, the method for inspection of a component further comprises archiving the image data and the feature for one or more of future damage progression detection, damage trending and condition-based maintenance.

In another and alternative embodiment, the method for inspection of a component further comprises controlling at least one of a position of at least one of the one or more controllable lights and an orientation of at least one of the one or more controllable lights, with respect to the component surface.

In another and alternative embodiment, the method for inspection of a component further comprises illuminating each of the at least one light in the array independently.

In another and alternative embodiment, the method for inspection of a component further comprises illuminating the component surface from multiple directions.

In another and alternative embodiment, the imaging device is configured as at least one of a high dynamic range camera and a multi-polarization camera.

In another and alternative embodiment, the method for inspection of a component further comprises computing a surface model from the image data to form a proxy model; and determining a feature based on dissimilarity between the image data and the proxy model.

An array of controllable lights are arranged around a part at low oblique angles. The position and orientation of the lights with respect to the part are controllable. The lights are triggered independently, in order to capture images, and detect defects from the cast shadows created by the lights. A model is registered and used to detect differences between the shadow images and the model. Examples of the model include an as-designed CAD model, an as-built model, a previous condition model and the like. As an alternative, a low-order surface model is computed from the data as a proxy to an a priori model. The differences from the proxy model and the captured shadow images can be computed.

Other details of the system and method for damage detection by cast shadows are set forth in the following detailed description and the accompanying drawings wherein like reference numerals depict like elements.

DETAILED DESCRIPTION

Figure 1:
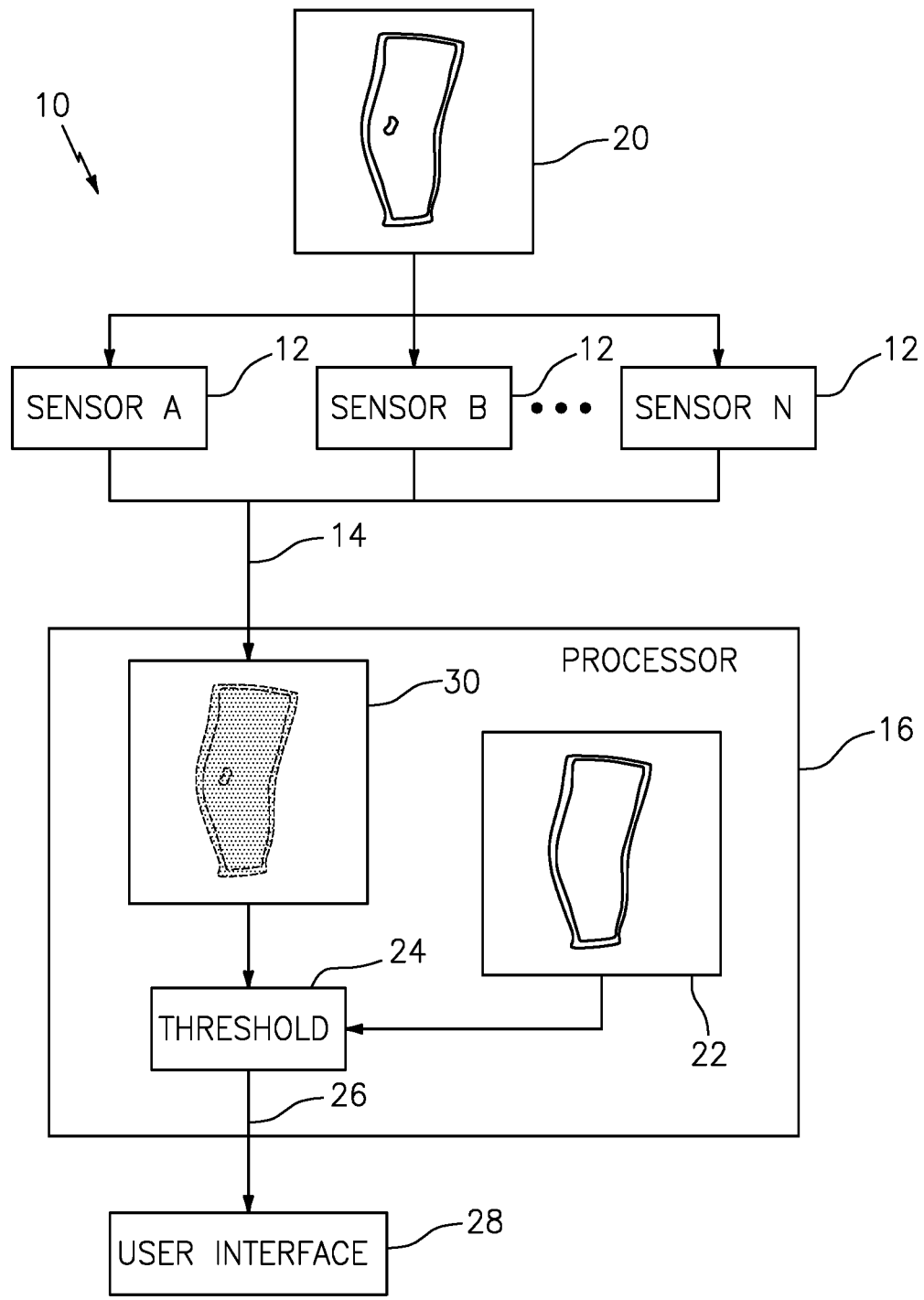
FIG. 1 is a schematic diagram of an exemplary inspection system in accordance with various embodiments.

Referring to FIG. 1, a schematic illustration of an automated inspection system 10 for detecting a defect or damage to a component 20 is shown, in accordance with various embodiments. The automated inspection system 10 may be configured to effectively perform 3D imaging of a component 20 and particularly for detection of coating imperfections. While component 20 may be any natural or manufactured object, in particular, it may include a component on an aircraft, such as an engine component, such as a fan or an airfoil (e.g., a fan, blade, or vane), a combustor liner, and the like. Component 20 may be scanned or sensed by one or more sensors 12 to obtain data 14 about the component 20. Data 14 may be obtained, for example, from a 1D or 2D sensor. In various embodiments, data 14 may be obtained by rotating, panning, or positioning the sensor(s) 12 relative to the component 20 to capture data 14 from multiple viewpoint angles, perspectives, and/or depths. Further, the component 20 may be rotated or positioned relative to the sensor(s) 12 to obtain data 14 from multiple viewpoints, perspectives, and/or depths. An array of sensors 12 positioned around component 20 may be used to obtain data 14 from multiple viewpoints. Thus, either of the sensor(s) 12 or component 20 may be moved or positioned relative to the other and relative to various directions or axes of a coordinate system to obtain sensor information from various viewpoints or perspectives, and/or depths. Further, sensor 12 may scan, sense, or capture information from a single position relative to component 20.

Figure 3:
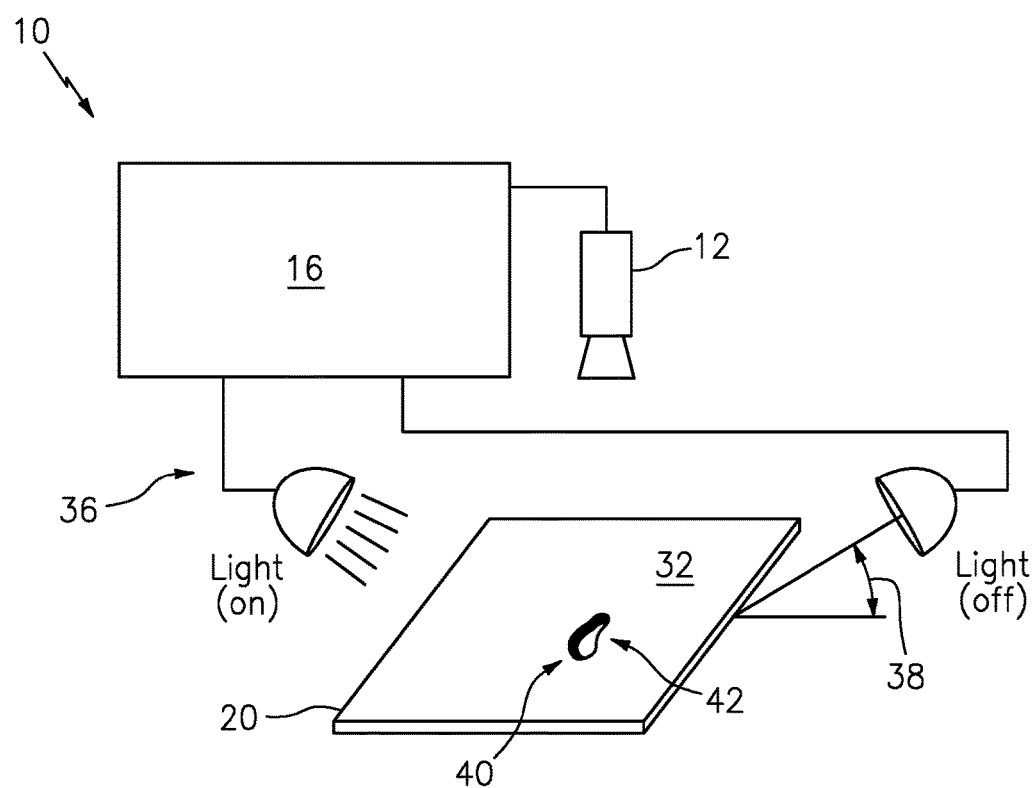
FIG. 3 is a schematic diagram of an exemplary inspection system.

A sensor 12 may include a one-dimensional (1D) or 2D sensor and/or a combination and/or array thereof. Sensor 12 may be operable anywhere in the electromagnetic spectrum compatible with illumination 36 (FIG. 3). Sensor 12 may provide various characteristics of the sensed electromagnetic spectrum including intensity, spectral characteristics, polarization, etc.

In various embodiments, sensor 12 may include an image capture device, such as an optical device having one or more optical lenses, apertures, filters, and the like. Exemplary image capture devices include a DSLR camera, a surveillance camera, a high-dynamic range camera, a mobile video camera, an industrial microscope, or other imaging device or image sensor, capable of capturing 2D still images or video images. Sensor 12 may include two or more physically separated cameras that may view a component from different angles, to obtain visual stereo image data.

In various embodiments, sensor 12 may include a line sensor, a linear image sensor, or other 1D sensor. Further, sensor 12 may include a 2D sensor. Automated inspection system 10 may synthesize 2D or 3D information from the 1D sensor data; and inspection system 10 may extract 1D information or synthesize 3D information from the 2D sensor data. The extraction may be achieved by retaining only a subset of the data such as keeping only that data that is in focus. The synthesizing may be achieved by tiling or mosaicking the data. Even further, sensor 12 may include a position and/or orientation sensor such as an inertial measurement unit (IMU) that may provide position and/or orientation information about component 20 with respect to a coordinate system or other sensor 12. The position and/or orientation information may be beneficially employed in aligning 1D, 2D or 3D information to a reference model as discussed elsewhere herein.

Data 14 from sensor(s) 12 may be transmitted to one or more processors 16 (e.g., computer systems having a central processing unit and memory) for recording, processing and storing the data received from sensors 12. Processor 16 may include a general-purpose processor, a digital signal processor (DSP), an application specific integrated circuit (ASIC), a field programmable gate array (FPGA) or other programmable logic device, discrete gate or transistor logic, discrete hardware components, or any combination thereof. Processor 16 may be in communication (such as electrical communication) with sensors 12 and may be configured to receive input, such as image information from sensors 12. Processor 16 may receive data 14 about component 20 captured and transmitted by the sensor(s) 12 via a communication channel. Upon receiving the data 14, the processor 16 may process data 14 from sensors 12 to determine if damage or defects are present on the component 20.

In various embodiments, processor 16 may receive or construct 3D information or image data 30 corresponding to the component 20. The 3D information may be represented as one or more 2D datasets. Processor 16 may further include a reference model 22 stored, for example, in memory of processor 16. Reference model 22 may be generated from a CAD model, a 3D CAD model, and/or 3D information, such as from a 3D scan or 3D information of an original component or an undamaged component. Reference model 22 may also be generated from the current data 14. Reference model 22 may be a theoretical model or may be based on historical information about component 20. Reference model 22 may be represented as one or more 2D datasets. Reference model 22 may be adjusted and updated as component 20 and/or similar components are scanned and inspected. Thus, reference model 22 may be a learned model of a component and may include, for example, 3D information including shape and surface features of the component.

In various embodiments, processor 16 of automated inspection system 10 may classify the damage and determine the probability of damage and/or if the damage meets or exceeds a threshold 24. Threshold 24 may be an input parameter based on reference model 22, based on user input, based on current data 14, and the like. Processor 16 may provide an output 26 to a user interface 28 indicating the status of the component 20. User interface 28 may include a display. The automated inspection system 10 may display an indication of the damage to component 20, which may include an image and/or a report. In addition to reporting any defects in the component, output 26 may also relay information about the type of defect, the location of the defect, size of the defect, etc. If defects are found in the inspected component 20, an indicator may be displayed on user interface 28 to alert personnel or users of the defect.

Figure 2:
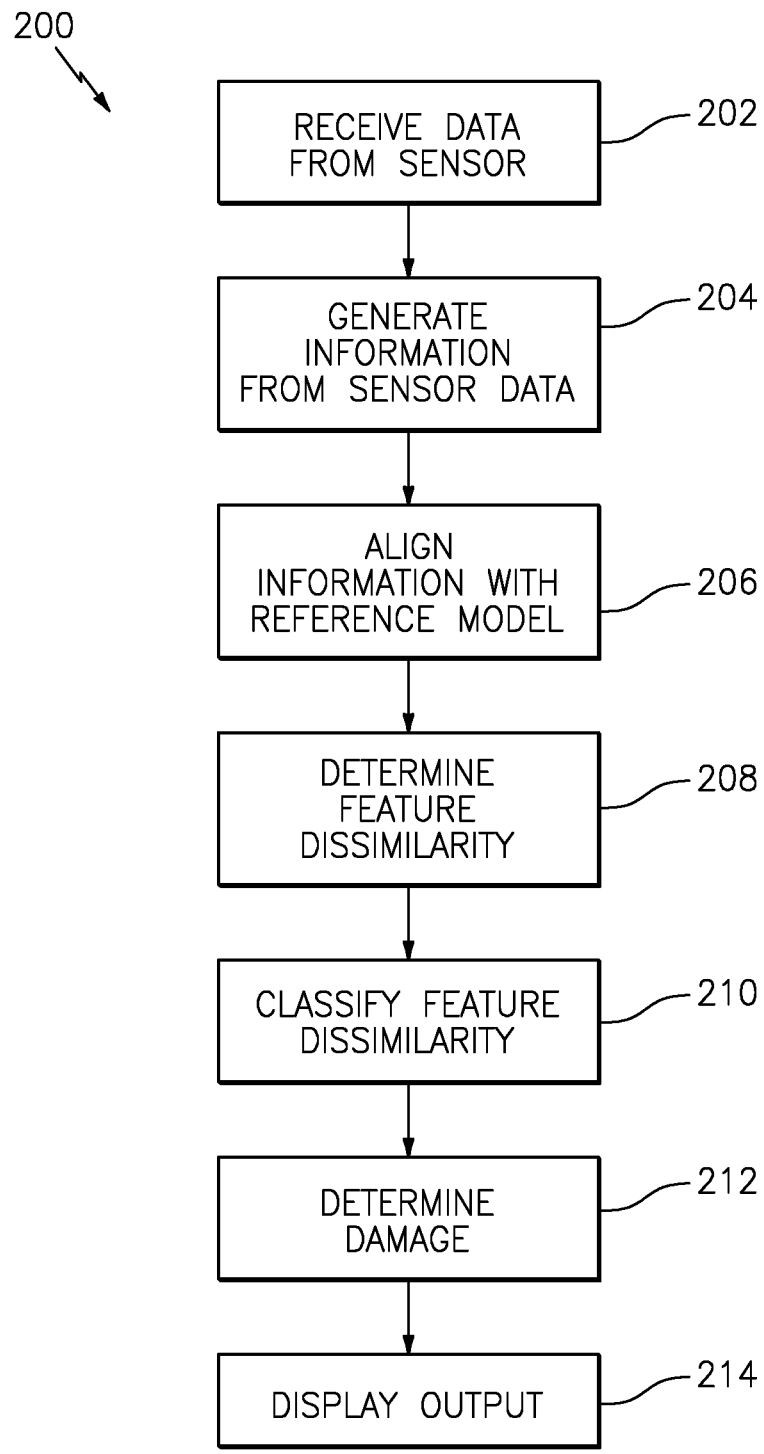
FIG. 2 is a process map of an exemplary inspection system in accordance with various embodiments.

With reference to FIG. 2, a method 200 for detecting defects is provided, in accordance with various embodiments. Processor 16 may be capable of carrying out the steps of FIG. 2. One or more sensors 12 may capture data about a component 20. Method 200, performed by processor 16 of automated inspection system 10, may include receiving data from a sensor/camera (step 202). Method 200 may include generating current condition information from the sensor data (step 204). The current condition information may correspond to the component. Method 200 may include aligning the current condition information with a reference model (step 206), determining a feature dissimilarity between the current condition information and the reference model (step 208), classifying the feature dissimilarity (step 210), determining damage (step 212), and displaying an output (step 214).

Step 202 may further comprise receiving 1D or 2D data from a sensor 12. In an exemplary embodiment, the entire forward surface of a gas turbine engine fan blade can be captured. In yet another exemplary embodiment, the entire pressure or suction surface of a turbine blade can be captured.

Step 204 may comprise constructing a complete image of component 20 by tiling or mosaicking information from one or more sensors 12 or multiple viewpoints. Step 204 may comprise merging data 14 from multiple viewpoints. In various embodiments, step 204 may comprise merging a first data from a 1D sensor and a second data from a 2D sensor and processing the 1D and 2D data to produce 3D information 30.

Step 206 may comprise aligning 2D current condition information with a reference model 22.

Step 206 may further comprise aligning the 3D information with a reference model 22, such as a 3D point cloud, by an iterative closest point (ICP) algorithm modified to suppress misalignment from damage areas of the component 20. The alignment may be performed by an optimization method, i.e., minimizing an objective function over a dataset, which may include mathematical terms in the ICP objective function or constraints to reject features or damage as outliers. The alignment may be performed by a 3D modification to a random sample consensus (RANSAC) algorithm, scale-invariant feature transform (SIFT), speeded up robust feature (SURF), other suitable alignment method. Step 206 may further include comparing the 3D information 30 to the reference model 22 to align the features from the 3D information 30 with the reference model 22 by identifying affine and/or scale invariant features, diffeomorphic alignment/scale cascaded alignment, and the like. Step 206 may further include registering the features.

Step 208 may further comprise computing features, such as surface and shape characteristics, of the component 20 by methods to identify and extract features. For example, processor 16 may determine differences or dissimilarities between the information 30 and the reference model 22. Step 208 may further comprise identifying features and determining differences or dissimilarities between the identified features in the information 30 and the reference model 22 using a statistical algorithm such as histogram of gradients (HoG), histogram of oriented gradients (HoOG), histogram of gradients in 3D (HoOG3D), a histogram of oriented gradients in 3D (HoOG3D), 3D Zernike moments, or other algorithms. In a HoOG3D method, processor 16 may define the orientation of edges and surfaces of information 30 by dividing the information 30 into portions or cells and assigning to each cell a value, where each point or pixel contributes a weighted orientation or gradient to the cell value. By grouping cells and normalizing the cell values, a histogram of the gradients can be produced and used to extract or estimate information about an edge or a surface of the component 20. Thus, the features of the information 30, such as surface and edge shapes, may be identified. Other algorithms, such as 3D Zernike moments, may similarly be used to recognize features in 3D information 30 by using orthogonal moments to reconstruct, for example, surface and edge geometry of component 20. Step 208 may further comprise determining differences or dissimilarities between the identified features in the information 30 and the reference model 22. The dissimilarities may be expressed, for example, by the distance between two points or vectors. Other approaches to expressing dissimilarities may include computing mathematical models of information 30 and reference model 22 in a common basis (comprising modes) and expressing the dissimilarity as a difference of coefficients of the basis functions (modes). Differences or dissimilarities between the information 30 and the reference model 22 may represent various types of damage to component 20.

Step 210 may further comprise classifying the feature dissimilarities identified in step 208. The automated inspection system 10 may include categories of damage or defect types for component 20. For example, damage may be categorized into classes such as warping, stretching, edge defects, erosion, nicks, cracks, and/or cuts. Step 210 may further comprise identifying the damage type based on the dissimilarities between the information 30 and the reference model 22. Step 210 may further comprise classifying the feature dissimilarities into categories of, for example, systemic damage or localized damage. Systemic damage may include warping or stretching of component 20. Localized damage may include edge defects, erosion, nicks, cracks, or cuts on a surface of component 20. Classifying the feature dissimilarities may be accomplished by, for example, support vector machine (SVM), decision tree, deep neural network, recurrent ensemble learning machine, or other classification method.

The detection of damage may include differencing the data and a model to produce an error map. The error map may contain small errors due to model-mismatch and sensing errors, and may contain large, spatially correlated errors where damage has occurred.

Step 212 may further comprise determining whether the feature difference or dissimilarity represents damage to component 20. Step 212 may comprise determining a probability of damage represented by the feature dissimilarity and/or classification. Step 212 may comprise determining damage by comparing the probability of damage to a threshold. Damage may be determined if the probability meets or exceeds a threshold. The automated inspection system 10 may determine if the damage is acceptable or unacceptable, and may determine if the component 20 should be accepted or rejected, wherein a rejected component would indicate that the component should be repaired or replaced.

Various types of damage such as missing material, cracks, delamination, creep, spallation, and the like can be detected automatically by using a deep learning classifier trained from available data, such as a library of user characterized damage examples, by using statistical estimation algorithms, by image or video classification algorithms, and the like. Deep learning is the process of training or adjusting the weights of a deep neural network. In an embodiment the deep neural network is a deep convolutional neural network. Deep convolutional neural networks are trained by presenting an error map or partial error map to an input layer and, a damage/no-damage label (optionally, a descriptive label, e.g., missing material, crack, spallation, and the like), to an output layer. The training of a deep convolutional network proceeds layer-wise and does not require a label until the output layer is trained. The weights of the deep network's layers are adapted, typically by a stochastic gradient descent algorithm, to produce a correct classification. The deep learning training may use only partially labeled data, only fully labeled data, or only implicitly labeled data, or may use unlabeled data for initial or partial training with only a final training on labeled data.

In another embodiment statistical estimation or regression techniques to determine if damage is present in the error map. Statistical estimation regression techniques can include principal components analysis (PCA), robust PCA (RPCA), support vector machines (SVM), linear discriminant analysis (LDA), expectation maximization (EM), Boosting, Dictionary Matching, maximum likelihood (ML) estimation, maximum a priori (MAP) estimation, least squares (LS) estimation, non-linear LS (NNLS) estimation, and Bayesian Estimation based on the error map.

Step 214 may further comprise transmitting, displaying, or storing the 2D or 3D information, feature differences or dissimilarities, classification of the feature differences or dissimilarities, a damage report, and/or a determination or recommendation that the component 20 be accepted or rejected. Step 214 may further comprise displaying an image, a model, a combined image and model, a 2D perspective from a model, and the like, of the damaged component for further evaluation by a user or by a subsequent automated system.

Referring also to FIG. 3 an exemplary automated inspection system 10 can be seen. In another exemplary embodiment, the system 10 can include an automated inspection system for detection of coating imperfections based on the method of "shape from shadows" for applications such as gas turbine engine blade coating inspection. The component 20 can be a blade of a fan, or a blade of a compressor, a blade of a turbine, a combustor liner, or other component with a surface coating. The exemplary embodiment shown in FIG. 3 includes a component 20 with a surface coating 32. The sensor 12 is shown as a camera 12 configured to capture images of a surface coating 32. The camera 12 can be a high dynamic range camera or a multi-polarization camera to capture the necessary image data 14 of the surface 32.

An array of controllable light(s) 36 are mounted at low oblique angles 38 around the component 20. The light(s) 36 may be operable anywhere in the electromagnetic spectrum compatible with sensor(s) 12. In particular, light(s) 36 and/or sensor(s) 12 may operate at any one frequency in the electromagnetic spectrum (monochromatic), one band of frequencies (polychromatic), or one or more combinations of the foregoing. Light(s) 36 and/or sensor(s) 12 may employ filters (not shown) to achieve operation in the desired frequencies and/or bands. In one non-limiting embodiment light(s) 36 and sensor(s) 12 operate at a frequency or frequencies outside the spectrum of ambient illumination such that ambient illumination does not interfere with light(s) 36 and sensor(s) 12. The array of light(s) 36 are configured to illuminate the component surface 32 and cast at least one shadow 40 to be detected as in a feature dissimilarity or simply feature 42 on the component surface 32. The feature 42 can result from a shallow surface defect, damage, crack, and the like formed on the surface 32. The processor 16 is coupled to the imaging device 12 and the array of light(s) 36. The array of light(s) 36 are arranged to illuminate the component surface 32 from multiple directions. The array of light(s) 36 can be controlled independently, such that, the light(s) 36 cast the shadows 40. The cast shadows 40 represent 3D information about the surface 32.

The processor 12 can be configured to determine damage to the coating 34 based on image or video analytics. The processor 16 can be configured to automatically report damage and archive the damage for trending and condition-based-maintenance.

The processor 16 can be configured to receive the data for the surface 32 of the component 20 from the imaging device 12. The processor 16 can be configured to perform operations like controlling the lighting array 36 to cast the shadows 40. The processor 16 can receive image data 30 for the component 20 from the imaging device 12. The processor 16 can determine a feature dissimilarity 42 between the image data 30 and a reference model 22. The processor 16 can classify the feature dissimilarity 42 and determine a probability that the feature dissimilarity 42 indicates damage to the component. The processor 16 can include operations to remove specular reflections. A specular reflection is a type of surface reflectance often described as a mirror-like reflection of light from the surface. In specular reflection, the incident light is reflected into a single outgoing direction. The processor 16 can include operations to control at least one of a position of at least one light in the array 36 and an orientation of at least one light in the array 36, with respect to the component surface 32. The processor 16 can include operations to illuminate each of the light(s) in the array independently. The processor 16 can include operations to illuminate the component surface from multiple directions. The processor 16 can include operations to compute a surface model from the image data to form a proxy model. The processor 16 can include operations to determine a feature dissimilarity between the image data and a proxy model.

There has been provided a system and method for damage detection by cast shadows. While the system and method for damage detection by cast shadows has been described in the context of specific embodiments thereof, other unforeseen alternatives, modifications, and variations may become apparent to those skilled in the art having read the foregoing description. Accordingly, it is intended to embrace those alternatives, modifications, and variations which fall within the broad scope of the appended claims.

What is claimed is:

1. An inspection system comprising:
   an imaging device mounted so as to image a component surface;
   at least one controllable light mounted at an oblique angle around said component and configured to illuminate said component surface and cast at least one shadow on said component surface; and
   a processor coupled to said imaging device and said at least one controllable light; said processor comprising a tangible, non-transitory memory configured to communicate with said processor, the tangible, non-transitory memory having instructions stored therein that, in response to execution by the processor, cause the processor to perform operations comprising:
   controlling, by the processor, said at least one controllable light to cast said at least one shadow;
   receiving, by the processor, image data for said component from said imaging device;
   removing, by the processor, specular reflections from the image data;
   determining, by the processor, a feature dissimilarity between the image data and a reference model;
   classifying, by the processor, the feature dissimilarity; and
   determining, by the processor, a probability that the feature dissimilarity indicates damage to the component.

2. The inspection system of claim 1, wherein said processor is further configured to control at least one of a position of the at least one light and an orientation of the at least one light, with respect to said component surface.

3. The inspection system of claim 2, wherein controlling, by the processor, said at least one light to cast said shadows further comprises:
   illuminating said at least one light independently.

4. The inspection system of claim 3, wherein controlling, by the processor, said at least one light to cast said shadows further comprises:
   illuminating said component surface from multiple directions.

5. The inspection system of claim 1, wherein said processor is further configured to compute a surface model from said image data to form a proxy model.

6. The inspection system of claim 1, wherein said processor is further configured to determine a feature based on a dissimilarity between the image data and a proxy model.

7. The inspection system of claim 6, wherein said feature comprises a surface defect.

8. The inspection system of claim 6, wherein said feature comprises a coating imperfection.

9. The inspection system of claim 1, wherein said imaging device is configured as at least one of a high dynamic range camera and a multi-polarization camera.

10. The inspection system of claim 1, further comprising: at least one filter associated with said at least one controllable light and said imaging device wherein said at least one filter provides attenuation to at least one of intensity, frequency, and polarization.

11. A method for inspection of a component, comprising:
    imaging a component surface with an imaging device;
    mounting at least one controllable light at an oblique angle around said component;
    illuminating said component surface;
    casting at least one shadow on said component surface;
    coupling a processor to said imaging device and said at least one controllable light; said processor comprising a tangible, non-transitory memory configured to communicate with said processor, the tangible, non-transitory memory having instructions stored therein that, in response to execution by the processor, cause the processor to perform operations comprising:
    controlling said at least one controllable light to cast said at least one shadow;
    receiving image data for said component from said imaging device;
    determining a feature dissimilarity between the image data and a reference model;
    classifying the feature dissimilarity; and
    determining a probability that the feature dissimilarity indicates damage to the component
    detecting a defect based on said at least one shadow; and
    archiving said image data and said feature dissimilarity for at least one of future damage progression detection, damage trending and condition-based maintenance.

12. The method for inspection of a component of claim 11, further comprising:
    controlling at least one of a position of said at least one light and an orientation of said at least one light, with respect to said component surface.

13. The method for inspection of a component of claim 12 further comprising:
    illuminating said at least one light independently.

14. The method for inspection of a component of claim 13, further comprising:
    illuminating said component surface from multiple directions.

15. The method for inspection of a component of claim 11, wherein said imaging device is configured as at least one of a high dynamic range camera and a multi-polarization camera.

16. The method for inspection of a component of claim 12, further comprising:
    computing a surface model from said image data to form a proxy model; and
    determining a feature based on dissimilarity between the image data and the proxy model.

* * * * *